US008359662B2

(12) United States Patent
Viljanen

(10) Patent No.: US 8,359,662 B2
(45) Date of Patent: Jan. 29, 2013

(54) PROTECTIVE DEVICE

(75) Inventor: Lasse Viljanen, Turku (FI)

(73) Assignee: Euromaski Oy, Rauma (FI)

(*) Notice: Subject to any disclaimer, the term of this patent is extended or adjusted under 35 U.S.C. 154(b) by 792 days.

(21) Appl. No.: 11/785,471

(22) Filed: Apr. 18, 2007

(65) Prior Publication Data

US 2007/0266484 A1 Nov. 22, 2007

(30) Foreign Application Priority Data

Apr. 20, 2006 (FI) ...................................... 20065246

(51) Int. Cl.
*A61F 9/06* (2006.01)
*A42C 5/04* (2006.01)
*A62B 18/02* (2006.01)

(52) U.S. Cl. .......................... 2/8.6; 2/171.3; 128/206.21

(58) Field of Classification Search ............... 2/410, 6.1, 2/6.2, 6.3, 6.4, 6.5, 6.6, 6.7, 6.8, 7, 8.1, 8.2, 2/8.3, 8.4, 8.5, 8.6, 8.7, 8.8, 422, 5; 128/201.22, 128/201.23, 201.24, 203.29, 206.21, 205.22, 128/205.25, 207.11

See application file for complete search history.

(56) References Cited

U.S. PATENT DOCUMENTS 1,646,103 A * 10/1927 Patrick ..................... 128/200.27
1,813,915 A * 7/1931 Cover ...................... 128/201.25
2,178,800 A * 11/1939 Lombard ................ 128/205.11
2,362,775 A * 11/1944 Sebouh .................... 128/201.11
2,376,871 A * 5/1945 Fink ......................... 128/201.19
5,538,000 A * 7/1996 Rudolph ................. 128/205.25
6,014,971 A * 1/2000 Danisch et al. .......... 128/201.25
6,044,844 A * 4/2000 Kwok et al. ............. 128/207.11
6,439,235 B1 8/2002 Larquet
6,615,828 B1 * 9/2003 Petherbridge ............ 128/200.28
6,889,689 B1 * 5/2005 Neuman .................. 128/201.22
7,370,652 B2 * 5/2008 Matula et al. ............ 128/206.11
7,735,490 B2 * 6/2010 Rinaldi .................... 128/207.18
8,091,553 B2 * 1/2012 Bordewick et al. ...... 128/207.11
2004/0226566 A1 * 11/2004 Gunaratnam et al. ... 128/207.18
2005/0076913 A1 * 4/2005 Ho et al. .................. 128/206.27
2005/0199242 A1 * 9/2005 Matula et al. ............ 128/207.13
2006/0081250 A1 * 4/2006 Bordewick et al. ...... 128/206.11
2007/0246043 A1 * 10/2007 Kwok et al. ............. 128/201.22

FOREIGN PATENT DOCUMENTS

EP 1 302 219 12/2005
FR 2 797 770 3/2001
WO WO 98/06458 2/1998

* cited by examiner

*Primary Examiner* — Shelley Self
*Assistant Examiner* — Jane Yoon
(74) *Attorney, Agent, or Firm* — Young & Thompson

(57) ABSTRACT

A protective device comprising a band part to be arranged on the wearer's head and a channel part arranged thereto and means for supplying air into the channel part and further through the end of the channel part to the wearer's facial area. The protective device further comprises a connecting part provided with two branch parts to be arranged at the end of the channel part, the ends of the branch parts being arranged to be connected to air supply means arranged in the mask part covering the wearer's mouth and nose.

7 Claims, 5 Drawing Sheets

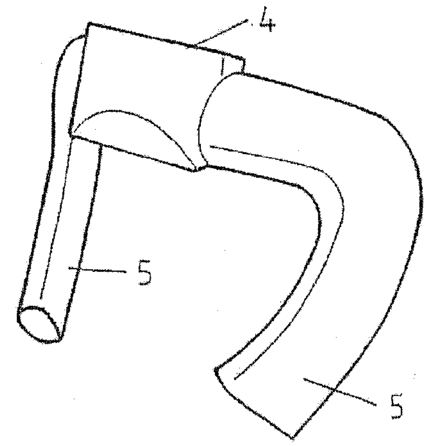
FIG. 2
FIG. 3
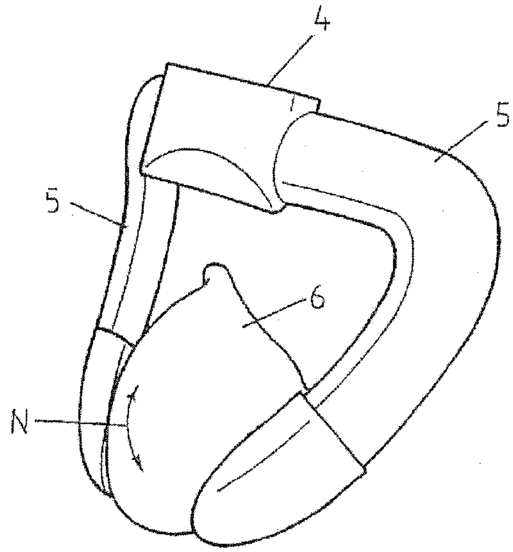
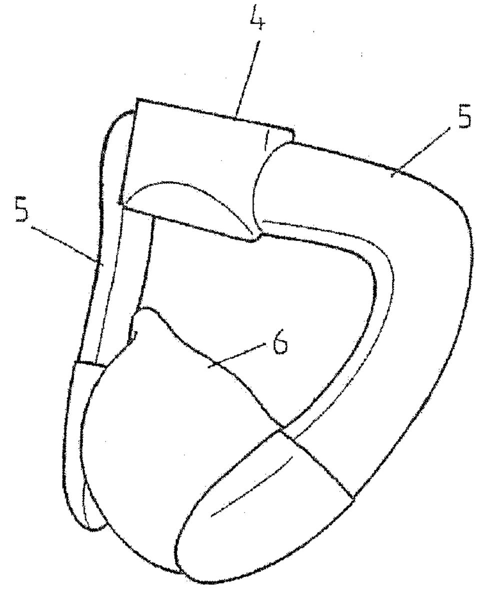
FIG. 4

PROTECTIVE DEVICE

The invention relates to a protective device comprising a band part to be arranged on the wearer's head, a channel part arranged thereto, and means for supplying air into the channel part and further through the end of the channel part to the wearer's facial area.

The above mentioned protective devices are currently well known in connection with various stages of operation, where owing to the working conditions fresh air must be supplied to the worker, for instance, for breathing. Examples of jobs, in which such situations are common include welding; grinding, finishing and various cleaning jobs. As regards the jobs mentioned above the working conditions are very often difficult, problems are caused by the high temperature in the environment and by gases and impurities in the surrounding air.

Attempts have been made to solve the above problem by means of different solutions. The solution shown in patent publication U.S. Pat. No. 6,443,153 can be referred to as an example of the typical prior art solutions.

The solutions known in the art, such as the solution shown in patent publication U.S. Pat. No. 6,443,153, basically operate as desired, but the draught created during the flow of supply air has constantly caused problems as well as the as been complicated to use. The problem associated with draught is created as some people are very sensitive to draught and in any case a continuous air flow to the same place irritates the skin, for instance, during long-lasting working situations. For this reason the solutions, in which air is blown inside a protective helmet using different nozzle solutions are not suitable for all. The problem is emphasized by the fact that the degree to which people are sensitive to draught varies greatly, meaning that the slightest draught is uncomfortable to some people whereas other people are practically insensitive to draught. The inconvenience of use, for instance the complexity of carrying out adjustment operations, easily leads to the protective device not being properly positioned and at the worst not being used at all.

It is an object of the present invention to provide a protective device that allows eliminating the drawbacks of the prior art. This is achieved with the protective device according to the invention. The protective device according to the invention is characterized in that the protective device comprises a connection part arranged at the end of a channel part, the connection part being provided with two branch parts, the ends of which are arranged to be connected to air supply means arranged in a mask part covering the wearer's mouth and nose.

An advantage of the protective device according to the invention compared with the known solutions is that the problems caused by draught can be eliminated very efficiently. The invention also allows for efficiently eliminating the problems associated with the inconvenient use of the prior art. Adjustments need not be made at all after the initial adjustments have been made, if the wearer of the device remains the same.

The invention will be explained in greater detail in the embodiment described in the accompanying drawing, in which FIG. 1 schematically shows a channel part to be used in the solution of the invention supported on the wearer's head;

FIG. 2 separately shows a component to be used in the solution of the invention comprising a connection part and branch parts;

FIG. 3 shows the component shown in FIG. 2 connected to a mask part;

FIG. 4 shows the entity shown in FIG. 3 while the mask part is placed in a different position;

Figure 5:
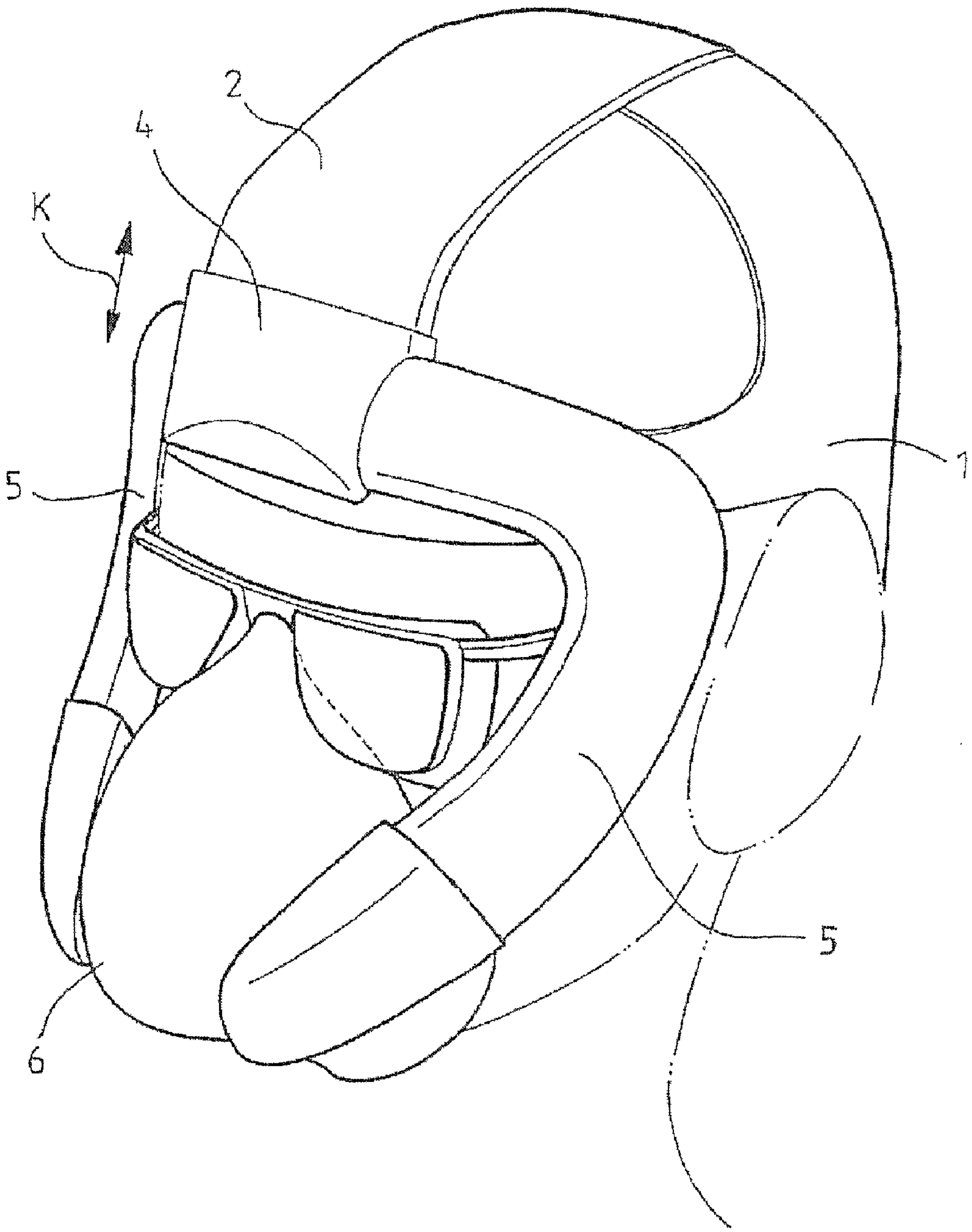
Figure 6:
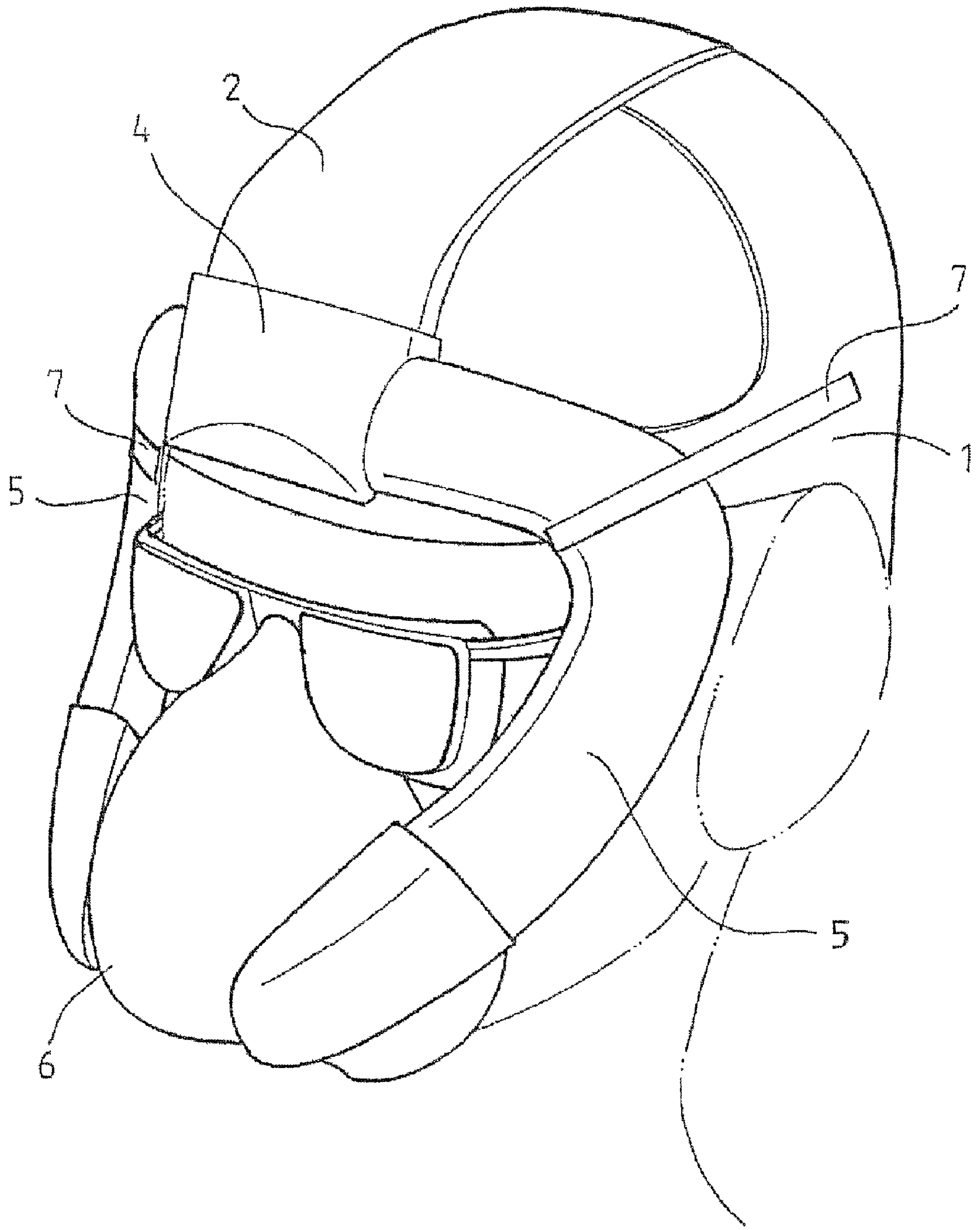
Figure 7:
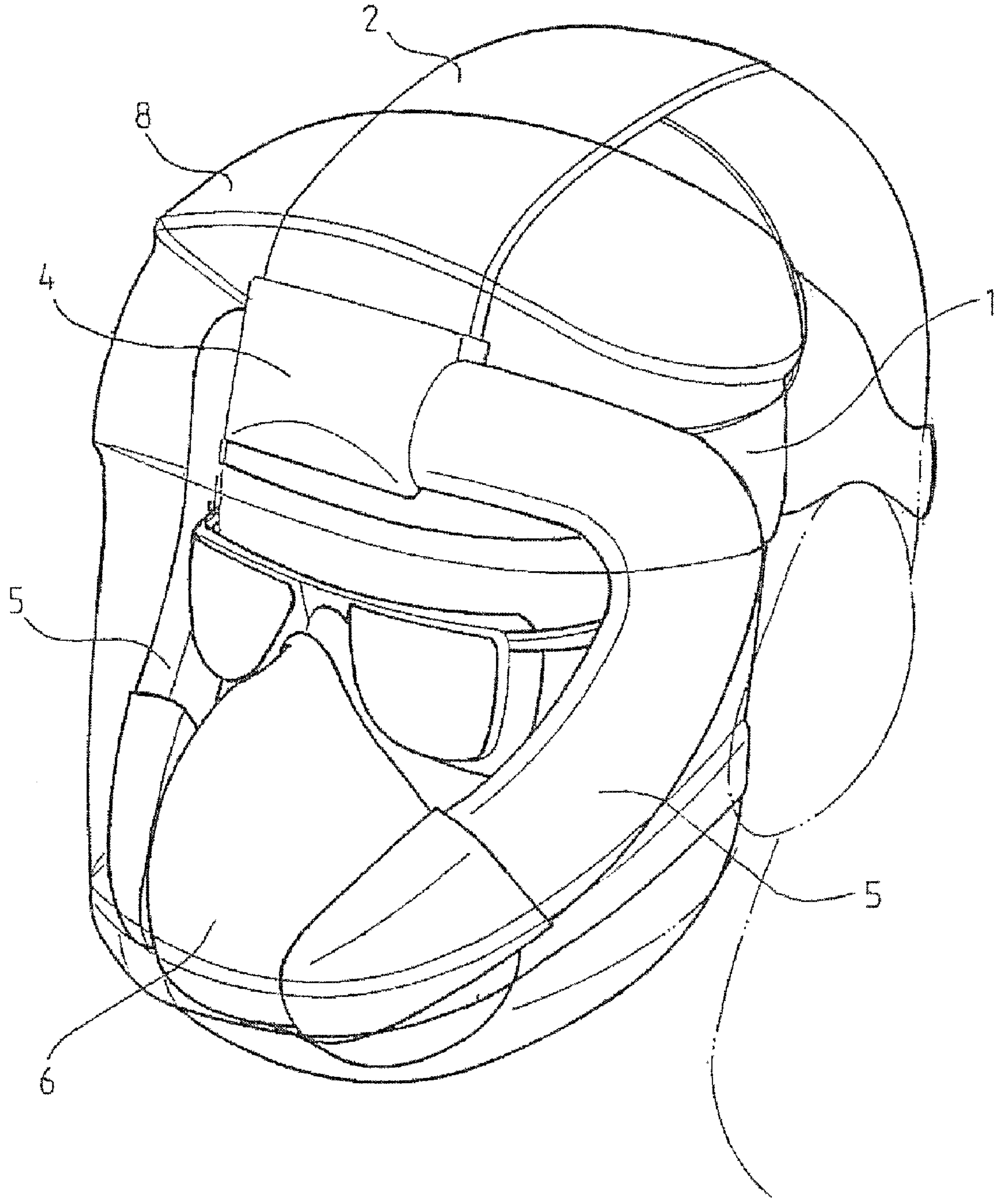

FIG. 5 schematically shows a protective device of the invention arranged on the wearer's head;

FIG. 6 shows the application shown in FIG. 5 provided with fastening parts between the branch parts and a band part, and FIG. 7 shows the application shown in FIG. 5 in a situation, in which the protective device according to the invention is used with a welding shield.

Figure 1:
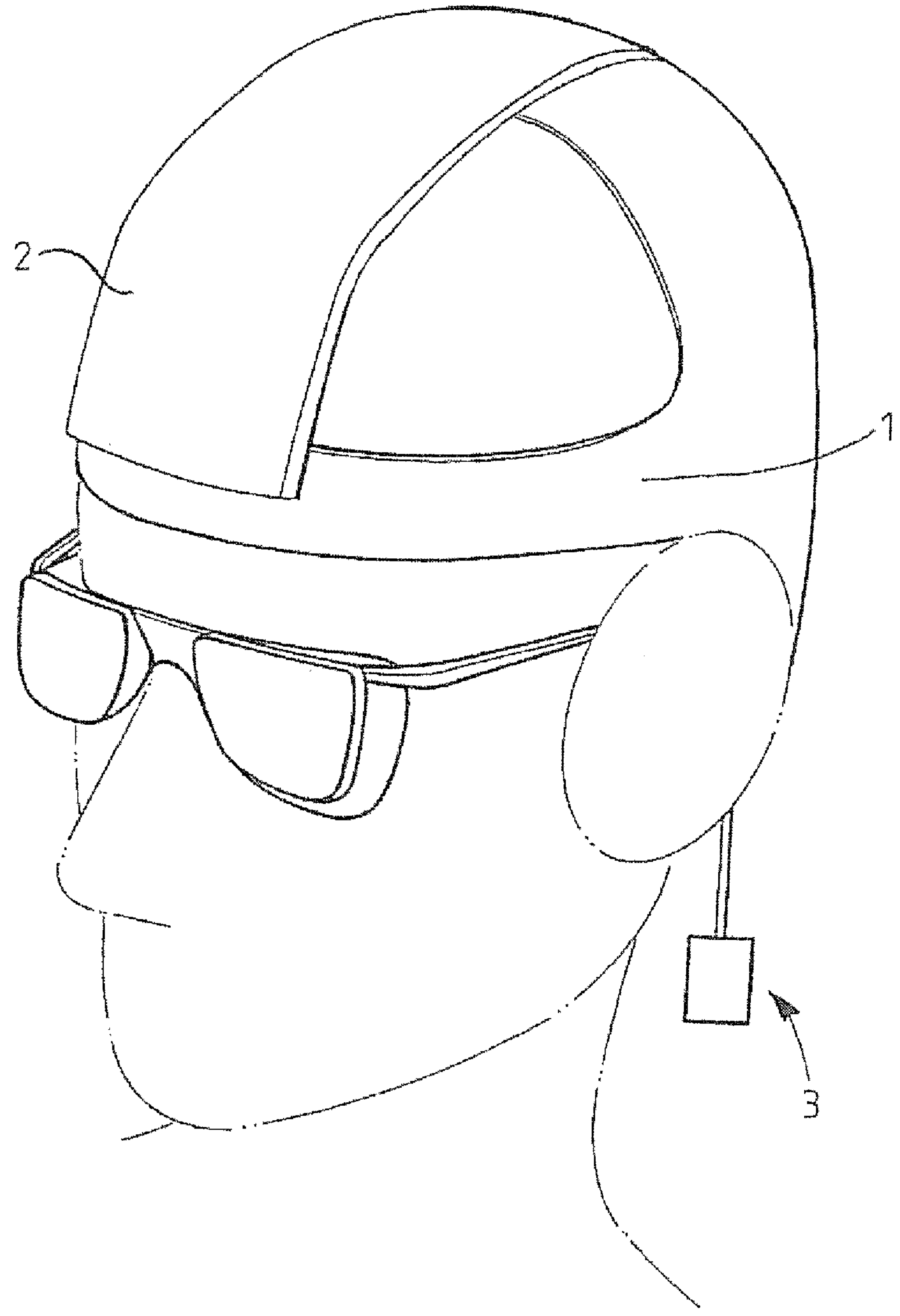

FIG. 1 schematically shows by means of a band part 1, and a channel part 2 arranged on the wearer's head. The channel part 2 may be provided with means for supplying air into the channel part 2 and further to the wearer's facial area through the end of the channel part. The means for supplying air into the channel part 2 are schematically shown in FIG. 1 with reference numeral 3.

The means 3 for supplying air may be formed of, for instance, a fresh air fan, which may be fastened to the wearer's back and connected to the channel part with an appropriate connecting pipe. The means 3 may also comprise a pressurized air system. The above described means represent a fully conventional technique for those skilled in the art, and therefore the means are not explained in more detail in this context.

In accordance with the essential idea of the invention, the protective device comprises a connecting part 4 provided with two branch parts 5 to be arranged at the end of the channel part 2. The branch parts 5 can preferably be arranged substantially on opposite sides of the connecting part 4 and be further arranged to project substantially in opposite directions from the connecting part 4 as shown in FIG. 2.

The ends of the branch parts 5 are arranged to be connected to air supply means, such as appropriate openings or valve elements, arranged in a mask part 6 covering the wearer's mouth and nose. What has proven to be a particularly preferable solution is one, in which the branch parts 5 are arranged to be adjustably fastened to the air supply means in the mask part 6 so that the position of the mask part 6 with respect to the branch parts is adjustable. The adjustment possibility referred to above is shown in FIGS. 3 and 4, in which the mask part 6 is in different positions in relation to the branch parts 5. The motion of the mask part is further shown schematically in FIG. 3 with arrow N. Owing to the above mentioned adjusting possibility the mask part 6 can be placed to tightly fit the shape of the wearer's face. The mask part 6 may refer to any appropriate mask part. An example of appropriate mask parts is the mask part described in EP patent publication 1 302 219 B1 that allows achieving a particularly preferable air supply with no draught.

The structure shown in FIGS. 2 to 4 is connected to the end of the channel part 2 as shown in FIG. 5. The connecting part 4 is fastened to the end of the channel part 2, in which case the connecting part is located in the wearer's forehead area and the branch parts 5 pass on both sides around the wearer's face substantially sideways to the mask part 6. This arrangement is clearly shown in FIG. 5.

It has proven to be particularly preferable to adjustably fasten the connecting part 4 to the end of the channel part 2 such that the location of the connecting part 4 with respect to the channel part 2 can be adjusted. The adjustment allows positioning the mask part 6 preferably at a correct location. The adjustment possibility referred to above is shown in FIG. 5 with arrow K.

The branch parts 5 can in accordance with the invention also be fastened to the band part 1 as shown in FIG. 6. Adjustable fastening parts may preferably be used as fastening parts 7, which may for instance be banded parts, such as adjustable fastening bands. The fastening parts 7 allow adjusting power, by which the mask 6 is pressed against the wearer's face. If the protective device is only used by a single wearer, as is often the case in practice, then the fastening parts 7 need not be adjusted more than once, in other words, when the device is adjusted to suit the wearer.

The protective device shown in FIGS. 1 to 6 is an independent respirator device, which allows controlling the respiratory air directly to the respirator zone without the problems caused by draught etc. The use of the protective device is easy and fast. In other words, when putting on the protective device, only the band part needs to be put on and tightened after the basic adjustments have been made, in which case the mask is automatically set and tightened in a correct position and tightness on the wearer's face.

The protective device according to the invention may appropriately be connected to be used with other protective devices, such as face shields and welding shields. FIG. 7 shows such an example. The welding shield is shown with reference numeral 8. The welding shield 8 can be fastened to a band part 1 in a totally conventional way. It is to be noted that the protection of respiration is maintained in this embodiment, although the welding shield 8 is lifted up. This is due to the fact that the protective device according to the invention is an independent device as shown above.

The embodiment described above is not in any way intended to restrict the invention, but the invention can be freely modified within the scope of the claims. It is therefore obvious that the protective device according to the invention or the details thereof need not necessarily have to be such as shown in the Figures, since other kinds of solutions are possible.

The invention claimed is:

1. A protective device comprising:

a band part to be arranged on a wearer's head and a channel part arranged thereto;

means for supplying air into the channel part and further through an end of the channel part to a wearer's facial area; and a connecting part provided with two branch parts to be arranged at the end of the channel part, the two branch parts being formed as continuous free-flow channels and ends of the branch parts being arranged to be connected to air supply means arranged in a mask part covering a wearer's mouth and nose, to supply all the air supplied by the means for supplying air into the mask part, wherein the channel part is arranged to pass over the wearer's head, the channel part being substantially rectangular and adapted to lay flat against the wearer's head and have a further protection device fitted on a flat top surface of the channel part, and the connecting part is arranged to be positioned on a wearer's forehead area and the branch parts are arranged to pass around the wearer's face substantially sideways to the mask part.

2. The protective device according to claim 1, wherein the branch parts are arranged substantially on opposite sides of the connecting part and arranged to project substantially in opposite directions from the connecting part.

3. The protective device according to claim 1, wherein the branch parts are arranged to be adjustably fastened to the air supply means provided in the mask part such that the position of the mask part in relation to the branch parts is adjustable.

4. The protective device according to claim 1, further comprising:

adjustable fastening parts, the adjustable fastening parts pressing the branch parts to the band part.

5. The protective device according to claim 4, wherein the adjustable fastening parts comprise banded parts.

6. The protective device according to claim 1, wherein the connecting part is adjustably arranged at the end of the channel part such that the position of the connecting part is adjustable in relation to the channel part.

7. A protective device comprising:

a band part to be arranged on a wearer's head and a channel part arranged thereto;

means for supplying air into the channel part and further through an end of the channel part to a wearer's facial area; and a connecting part provided with two branch parts to be arranged at the end of the channel part, the two branch parts being formed as continuous free-flow channels and ends of the branch parts being arranged to be connected to air supply means arranged in a mask part covering a wearer's mouth and nose, to supply all the air supplied by the means for supplying air into the mask part, wherein the channel part is arranged to pass over the wearer's head, the channel part being substantially rectangular and adapted to lay flat against the wearer's head and have a further protection device fitted on a flat top surface of the channel part, and the connecting part is arranged to be positioned on a wearer's forehead area and the branch parts are arranged to pass around the wearer's face substantially sideways to the mask part, and wherein a face shield or a welding shield is fastened to the band part.

* * * * *